United States Patent
Di Maio et al.

(10) Patent No.: US 11,471,501 B2
(45) Date of Patent: Oct. 18, 2022

(54) PHARMACEUTICAL COMPOSITION FOR USE IN THE TREATMENT OF PROSTATE PATHOLOGIES

(71) Applicant: NEILOS S.R.L., Piano di Sorrento (IT)

(72) Inventors: Umberto Di Maio, Piano di Sorrento (IT); Antonino Bagnulo, Piano di Sorrento (IT)

(73) Assignee: NEILOS S.R.L., Piano di Sorrento (IT)

(*) Notice: Subject to any disclaimer, the term of this patent is extended or adjusted under 35 U.S.C. 154(b) by 75 days.

(21) Appl. No.: 16/322,845

(22) PCT Filed: Jul. 27, 2017

(86) PCT No.: PCT/IB2017/054559
§ 371 (c)(1),
(2) Date: Feb. 1, 2019

(87) PCT Pub. No.: WO2018/025129
PCT Pub. Date: Feb. 8, 2018

(65) Prior Publication Data
US 2021/0379137 A1    Dec. 9, 2021

(30) Foreign Application Priority Data
Aug. 3, 2016   (IT) .................. 102016000081379

(51) Int. Cl.
| | | |
|---|---|---|
| A61K 31/00 | (2006.01) | |
| A61K 36/889 | (2006.01) | |
| A61P 13/08 | (2006.01) | |
| A61K 31/01 | (2006.01) | |
| A61K 31/12 | (2006.01) | |
| A61K 33/04 | (2006.01) | |
| A61K 33/30 | (2006.01) | |
| A61K 38/48 | (2006.01) | |

(52) U.S. Cl.
CPC ............ *A61K 36/889* (2013.01); *A61K 31/01* (2013.01); *A61K 31/12* (2013.01); *A61K 33/04* (2013.01); *A61K 33/30* (2013.01); *A61K 38/4873* (2013.01); *A61P 13/08* (2018.01)

(58) Field of Classification Search
CPC .................................................... A61K 31/00
See application file for complete search history.

(56) References Cited

U.S. PATENT DOCUMENTS

2005/0118282 A1   6/2005 Castor
2005/0260285 A1*  11/2005 DiMateeo-Leggio ..................... A61K 36/539
                                                                  424/725

FOREIGN PATENT DOCUMENTS

| WO | 2004/052351 A1 | 6/2004 |
| WO | 2005/004889 A1 | 1/2005 |
| WO | 2009/070818 A1 | 6/2009 |

OTHER PUBLICATIONS

English machine translation of Changzhou Adam Biotech Inc., CN 105106520 A, 2015.*
Zhulenko et al., "Pharmacology: textbooks and manuals for higher education students," Ministry of Agriculture of the Russian Federation,—Moscow: KolosS, 2008, pp. 34-35 (2 pages).
Altavilla et al., "The Combination of Serenoa Repens, Selenium and Lycopene is More Effective Than Serenoa Repens Alone to Prevent Hormone Dependent Prostatic Growth," *The Journal of Urology* 186:1524-1529, 2011.
Cai et al., "*Serenoa repens* associated with *Urtica dioica* (ProstaMEV®) and curcumin and quercetin (FlogMEV®) extracts are able to improve the efficacy of prulifloxacin in bacterial prostatitis patients: results from a prospective randomized study," *International Journal of Antimicrobial Agents* 33:549-553, 2009.
Dedhia et al., "Phytotherapy for Lower Urinary Tract Symptoms Secondary to Benign Prostatic Hyperplasia," *The Journal of Urology* 179:2119-2125, 2008.
Goodarzi et al., "The Efficacy of Zinc for Treatment of Chronic Prostatitis," *Acta Medica Indones.—Indones. J. Intern. Med.* 45(4):259-264, 2013.
Ilic et al., "Lycopene for the prevention and treatment of benign prostatic hyperplasia and prostate cancer: A systematic review," *Maturitas* 72:269-276, 2012.
Kim et al., "Inhibitory effect of curcumin on testosterone induced benign prostatic hyperplasia rat model," *BMC Complementary and Alternative Medicine* 15(380):1-7, 2015.
Kim et al., "Pathogenic role of HIF-1α in prostate hyperplasia in the presence of chronic inflammation," *Biochimica etBiophysica Acta* 1832:183-194, 2013.
Minutoli et al., "Inhibitors of apoptosis proteins in experimental benign prostatic hyperplasia: effects of serenoa repens, selenium and lycopene," *Journal of Biomedical Science* 21(19):1-8, 2014.

* cited by examiner

*Primary Examiner* — Rosanne Kosson
(74) *Attorney, Agent, or Firm* — Seed IP Law Group LLP

(57) ABSTRACT

The present invention relates to a pharmaceutical composition for use in the treatment of prostate pathologies. The present invention further relates to a composition comprising a mixture which comprises or, alternatively, consists of an effective amount of *Serenoa repens*, Bromelain, Curcumin, Zinc, Lycopene and Selenium, and pharmaceutically acceptable or food grade technological excipients and/or additives. The present invention further relates to a pharmaceutical composition, preferably in the form of softgel capsules, for use in the treatment of disorders or diseases or pathologies connected to and/or deriving from prostatitis and/or benign prostatic hyperplasia.

16 Claims, No Drawings

PHARMACEUTICAL COMPOSITION FOR USE IN THE TREATMENT OF PROSTATE PATHOLOGIES

The present invention relates to a pharmaceutical composition for use in the treatment of prostate pathologies. The present invention further relates to a composition comprising a mixture which comprises or, alternatively, consists of an effective amount of *Serenoa repens*, Bromelain, Curcumin, Zinc, Lycopene and Selenium, and pharmaceutically acceptable or food grade technological excipients and/or additives. The present invention further relates to a pharmaceutical composition, preferably in the form of softgel capsules, for use in the treatment of disorders or diseases or pathologies connected to and/or deriving from prostatitis and/or benign prostatic hyperplasia.

Diseases of prostatic tissue are well known. Prostatitis is one of the most widespread pathologies in the urological field. It is the most common urological problem in young men and becomes even more common after 50 years of age. Unfortunately, not much is known about the etiology of prostatitis, so it is often difficult to determine the most suitable therapy for treating this pathology. Prostatitis is classified into:

Category I: acute prostatitis of bacterial origin.
Category IIa: chronic prostatitis of bacterial origin;
Category IIb: chronic prostatitis of non-bacterial origin;
Category III: chronic pelvic pain syndrome;
Category IV: asymptomatic prostatitis.

Acute prostatitis of bacterial origin is characterised by a sudden onset of fever and dysuria. It must be treated with antibiotic therapy and any alternative therapy of a herbal type is inadvisable, since it could lead to a delay in the start of antibiotic therapy and this would lead to greater difficulties in removing the pathogenic agent.

Category II chronic prostatitis is characterised by recurrent urinary tract infections caused by bacteria that are localised in the prostate. The main etiologic agents are Gram-negative bacteria, such as *E. coli* and *Enterobacter*, or Gram-positive ones such as coagulase-negative staphylococci. Other microorganisms, such as *ureaplasma, chlamydia* and *mycoplasma* have been found in the prostatic fluid and urethra of men suffering from chronic prostatitis, but no direct correlation has yet been found between the presence of these microorganisms and the development of the pathology.

Most of the reported cases of prostatitis belong to category III, i.e. chronic pelvic pain syndrome (CP/CPPS). Type III prostatitis, called CP/CPPS (chronic prostatitis/chronic pelvic pain syndrome) is characterised by pelvic pain, urinary symptoms and painful ejaculation and there is often no documented infection of the urinary tract by uropathogens. The syndrome can be devastating, affects 10-15% of the male population and results in nearly 2 million outpatient visits a year. This form of prostatitis, in addition to being the most common, is the most enigmatic: it is often characterised by an absence of infection, though in some cases it can be triggered by bacterial infections, and at the same time it shows the signs of chronic inflammation or of an autoimmune disease. Even in the absence of an increase in the plasma levels of white blood cells, the prostatic secretions and seminal fluid of patients suffering from category III chronic prostatitis contain elevated concentrations of pro-inflammatory cytokines and molecules deriving from oxidative stress. A significant limitation to defining the molecular mechanisms of CP/CPPS is that the cause of the condition is largely unknown. It is believed that promoter events, such as infection or trauma, may lead to acute inflammation of the prostatic tissue, which later becomes chronic and leads to the development of chronic pelvic pain syndrome. The most frequently prescribed therapy in the case of prostatitis is an antibacterial one. Given that in order to reach the prostatic tissue, the antibacterial must be able to pass the "blood-prostate" barrier, whose permeability is not altered by the infection, it is necessary for the antibacterial to have a low molecular weight, high $pK_a$ and a high log P value, hence high lipophilia. The classes of antibacterials that fall into this category are quinolones, sulphamides, macrolides and tetracyclines. The first therapeutic measure often consists in 4-6 weeks of fluoroquinolones, which is effective in 50% of the men who start therapy upon the first appearance of symptoms.

Since the characteristic common to all categories of prostatitis is inflammation, steroidal and non-steroidal anti-inflammatory drugs are often prescribed. There are no doubts as to the effectiveness of these therapeutic agents in reducing the pain associated with the inflammation that is present in the case of prostatitis.

The problem is that these therapeutic agents are associated with numerous side effects. Non-steroidal anti-inflammatory drugs can lead to gastrointestinal ulceration and bleeding, liver and kidney dysfunctions and skin reactions. The side effects associated with the use of glucocorticoids are the following: dermatitis, teleangectasia, muscular atrophy, myopathy, osteoporosis, cataract, Cushing's syndrome, diabetes mellitus and effects on the cardiovascular system.

Thus there is still a felt need among practitioners in the field to be able to have a treatment for prostatitis, and more in general prostatic pathologies, which is effective on the one hand and free of the side effects present in the known treatments on the other.

Benign prostatic hyperplasia (BPH) is known. Benign prostatic hyperplasia is one of the most widespread urinary tract pathologies in individuals of the male sex. Onset generally occurs after 40 years of age and its incidence is directly proportional to age, being 50% at the age of 60 and 90% at the age of 85. Benign prostatic hyperplasia is characterised by high morbidity and low mortality and is considered a public health problem.

Two stages are distinguished in this pathology: the initial stage is asymptomatic and regards above all the periurethral zone, while the more advanced stage, also known as the clinical stage, is the one in which the enlarged prostate gland compresses the walls of the urethra, leading to an increase in resistance to urinary flow and sometimes to the presence of inflammation (prostatitis). This condition causes symptoms associated with a clinical picture known as "prostatism", which is characterised by static and dynamic components. The former regard stromal tissue and are due to an increase in the tone of the smooth muscle of the bladder neck and the stromal prostatic portion. The obstructive symptoms induced by dynamic components are represented by: post-micturition dribbling of urine, a sensation of incomplete bladder emptying, urinary retention, reduced velocity and force of the urinary flow and urinary intermittence. The static components of the clinical form of BPH (benign prostatic hyperplasia) are nycturia, incontinence, haematuria, urinary urgency and increased frequency of urination. The previously described symptoms can lead to anxiety, sleep disorders, sexual dysfunctions and a compromised sense of well-being, which can lead to interruptions in working activity and social relations, with a very negative impact on quality of life (QoL).

The origin of benign prostatic hyperplasia has not yet been clearly defined. Three theories about its pathogenesis have been proposed. The first theory is based on the role of androgens, estrogens and growth factors. The second theory on the pathogenesis of BPH is based on the presence of a small percentage of androgen-independent prostate cells that can renew themselves under conditions in which androgens are absent. Finally, the third theory regards the interactions between the stroma and prostate epithelium.

The treatment of this pathology (BPH) depends on the individual and the severity of the symptoms. Initially, in the less advanced stages of the pathology, it is sufficient to undergo frequent checks on the prostate and change one's lifestyle. When the symptoms worsen, one can move on to a pharmacological therapy or the use of medicinal plants.

The two main classes of drugs used to treat benign prostatic hyperplasia (BPH) are aradrenergic receptor antagonists (prazosin, terazosin, doxazosin, alfuzosin, tamsulosin, silodosin) and 5α-reductase inhibitors (finasteride, dutasteride), often used effectively in combination as a prophylactic therapy against the further progression of this pathology.

Because of the numerous and sometime serious side effects of the previously described classes of drugs and in view of the high morbidity and long latency of this pathology, there is a felt need among practitioners in this field to be able to have a treatment for benign prostatic hyperplasia (BPH) which is effective on the one hand and free of the side effects present in the known treatments on the other.

There is thus a felt need to be able to have a pharmaceutical composition for use in the treatment of prostate pathologies. Furthermore, there is a felt need to be able to have compositions for use in the treatment of disorders or diseases or pathologies connected to and/or deriving from prostatitis and/or benign prostatic hyperplasia (BPH).

After a long, intense research and development activity, the Applicant has identified and devised a combination (mixture) of compounds and substances that are capable of acting effectively, in a synergistic manner, against disorders or diseases or pathologies connected to and/or deriving from prostatitis and/or benign prostatic hyperplasia (BPH).

Advantageously, said combination (mixture) of compounds and substances is well tolerated and has no side effects, even if administered for extended periods in the form of a composition for oral use, for example a pharmaceutical composition in the form, for example, of softgel capsules.

Advantageously, said combination (mixture) of compounds and substances in the form of a composition for oral use, e.g. a pharmaceutical composition in the form, for example, of softgel capsules, is well tolerated when used on its own or in association/combination with pharmacological and/or surgical treatments.

The present invention relates to a composition comprising a mixture which comprises or, alternatively, consists of compounds and substances, and pharmaceutically acceptable or food grade technological excipients and/or additives, having the features as defined in the appended claim.

The present invention relates to a pharmaceutical composition for use as a medication comprising a mixture which comprises or, alternatively, consists of compounds and substances, and pharmaceutically acceptable or food grade technological excipients and/or additives, having the features as defined in the appended claim.

The present invention relates to a composition for use in the treatment of disorders or diseases or pathologies connected to and/or deriving from prostatitis and/or benign prostatic hyperplasia, said composition being comprised of a mixture which comprises or, alternatively, consists of compounds and substances, and pharmaceutically acceptable or food grade technological excipients and/or additives, having the features as defined in the appended claim.

Preferred embodiments of the present invention are illustrated below, without any intention of limiting the scope thereof.

The Applicant has devised and perfected a mixture of compounds and substances that together perform a synergistic activity. Said synergistic activity is obtained when the compounds and substances are administered all together simultaneously either in a single form of administration—unitary or monolithic—or, alternatively, when said compounds and said substances are administered separately in a sequential manner over time.

Unless specified otherwise, within the scope of the present invention the percentages and amounts of a component in a mixture are intended to refer to the weight of that component relative to the total weight of the mixture.

Unless specified otherwise, within the scope of the present invention, in relation to ranges of numerical values for a certain feature, the indication "from X to Y" comprises the extremes, i.e. X and Y, as well as all the possible intermediate numerical values.

In the context of the present invention, the term "composition(s)" is meant to include a pharmaceutical composition, a composition for a food supplement, a composition for a food product or a composition for a medical device.

In the context of the present invention, the term "medical device" is used with the meaning according to Italian Legislative Decree no. 46 of 24 Feb. 1997 and Directive 93/42/EEC of 14 Jun. 1993, i.e. it indicates a substance or another product, whether used alone or in combination, intended by the manufacturer to be used for human beings for the purpose of diagnosis, prevention, monitoring, treatment or alleviation of disease, and which does not achieve its principal intended action in or on the human body for which it is intended by pharmacological, immunological or metabolic means, but which may be assisted in its function by such means.

In one embodiment, the mixture of compounds and substances comprises or, alternatively, consists of: *Serenoa repens* (W. Batram) Small., Bromelain (term that relates to two proteolytic enzymes identified in *Ananas comosus*—family Bromeliaceae), Curcumin (*Curcuma longa*), Zinc, Lycopene and Selenium. By way of example, the ingredients making up the mixture of the present invention are described: the *Serenoa repens* is preferably obtained by supercritical extraction from fruit titrated to at least 90% in a sterolic lipid extract, the Lycopene is preferably from the fruit of *Solanum lycopesicum*, the Bromelain is preferably used as such or is extracted from the stem of *Ananas comosus* L. Merr., the Zinc can preferably be zinc oxide or zinc gluconate or zinc acetate, the Curcumin is preferably obtained from the rhizome of *Curcuma Longa* and the Selenium can preferably be Selenomethionine or from sodium selenite.

The *Serenoa repens* (W. Batram) Small. has an antiinflammatory and antioedemigenic effect.

Bromelain is a mixture of proteolytic enzymes extracted from pineapples. Bromelain has shown to possess various interesting activities from a pharmacological viewpoint, including: inhibition of platelet aggregation, reduction in the intensity of angina pectoris, treatment of bronchitis, sinusitis and thrombophlebitis and increase in the absorption of various active ingredients. The mechanism of action of Bromelain is supposed to consist in the following activities:

a) Increase in fibrinolytic activity; b) Reduction in plasma levels of fibrinogen; c) Reduction in levels of bradykinin (with a reduction in vascular permeability, reduction in oedema and pain); d) Reduction in the levels of $PGE_2$; e) Reduction in the levels of $TXA_2$; f)

Modulation of the adhesion of some cells of the immune system.

Studies on the effectiveness of Bromelain in the treatment of prostatitis or prostate pathologies in general do not presently exist; nevertheless, the Applicant believes that its anti-inflammatory activity may be useful in the treatment of these pathologies, as well as in the treatment of benign prostatic hyperplasia (BPH).

Curcumin is a product of natural origin mainly endowed with anti-inflammatory activity. Curcumin might be useful in the treatment of prostatitis and benign prostatic hyperplasia.

One of the main problems with Curcumin is its low oral bioavailability, due to its poor solubility. Zinc exhibits antioxidant and also antimicrobial properties. Moreover, zinc contributes to modulating testosterone levels.

Lycopene exhibits antioxidant and anti-proliferative activity, being capable of increasing the percentage of cells in the G0/G1 quiescent state and of inhibiting the family of the IGFs. The use of lycopene, therefore, might be useful in countering the onset of benign prostatic hyperplasia and prostate cancer, which can be caused, among the various factors, also by oxidative damage to DNA induced by ROSs (reactive oxygen species) during the inflammatory process.

Selenium has anti-inflammatory and antioxidant activity.

Furthermore, it is capable of inhibiting cell proliferation and promoting apoptosis.

The Applicant has found that the mixture of compounds and substances and, consequently, the composition of the present invention that contains them, both show an advantageous effect in the treatment of disorders or diseases or pathologies connected to and/or deriving from prostatitis and/or benign prostatic hyperplasia. The advantageous effect is obtained when the dose of the mixture (which corresponds to the amount by weight of the individual compounds and substances present in the mixture) contained in the composition of the present invention, preferably said composition being in the form of softgel capsules, and said mixture has the following features, on their own or in combination:

i) *Serenoa repens* (W. Batram) Small. is present in an amount by weight comprised from 200 mg to 600 mg, preferably 300 mg to 500 mg, even more preferably 400 mg, and/or ii) Bromelain is present in an amount by weight comprised from 10 mg to 400 mg, preferably 120 mg to 180 mg, even more preferably 150 mg, and/or iii) Curcumin is present in an amount by weight comprised from 50 mg to 500 mg, preferably 75 mg to 150 mg, even more preferably 100 mg, and/or iv) Zinc is present in an amount by weight comprised from 10 mg to 20 mg, preferably 12 mg to 18 mg, even more preferably 15 mg, and/or v) Lycopene is present in an amount by weight comprised from 1 mg to 10 mg, preferably 3 mg to 8 mg, even more preferably 6 mg, and/or vi) Selenium is present in an amount by weight comprised from 20 µg to 100 µg, preferably 40 µg to 60 µg, even more preferably 45 µg.

Embodiments of the mixture of compounds and substances of the present invention are the following (Table 1):

TABLE 1

| Active ingredient | 1-Dose | 2-Dose | 3-Dose | 4-Dose |
|---|---|---|---|---|
| *Serenoa repens*, phytosterolic extract | 400 mg | 300 mg | 450 mg | 500 mg |
| Bromelain | 150 mg | 250 mg | 200 mg | 120 mg |
| Curcumin | 100 mg | 150 mg | 100 mg | 75 mg |
| Zinc | 15 mg | 20 mg | 15 mg | 10 mg |
| Lycopene | 6 mg | 8 mg | 8 mg | 6 mg |
| Selenium | 41.5 µg | 50 µg | 40 µg | 41.5 µg |

Advantageously, the preferred dose is the one having the features indicated as 1-dose.

The composition containing the mixture of compounds and substances of the present invention enables at least one of the following effects/advantages to be obtained: (a) an antiandrogenic and antiproliferative effect, and/or (b) anti-inflammatory effect, and/or (c) antioxidant effect and/or (d) myorelaxant effect.

The *Serenoa repens* extract exhibits an inhibitory activity against 5α-reductase, which reduces the concentration of dihydrotestosterone, resulting in an antiproliferative activity due to the lower expression, at the level of the prostate, of growth factors, which would promote the proliferation of prostate cells. In addition to the antiproliferative action, it also exhibits a pro-apoptotic activity, thanks to its ability to inhibit the expression of anti-apoptotic proteins and increase the activity of caspase, resulting in a further blocking of cell proliferation. Lycopene is capable of acting as an androgen receptor antagonist, thus performing an antiandrogenic activity, but with a mechanism of action differing from that of *Serenoa repens*: for this reason, the two active ingredients are endowed with a synergistic action. Selenium exhibits antiproliferative activity, which can be complementary to the antiandrogenic activity (which results in the inhibition of growth factor expression) of *Serenoa repens* and Lycopene. Zinc, too, is endowed with antiandrogenic activity and acts synergistically with *Serenoa repens*, Selenium and Lycopene.

The liposterolic extract of *Serenoa repens* can inhibit the expression of various mediators of inflammation and is capable of directly inhibiting the activity of phospholipase A2, with a consequent reduction in the synthesis of prostaglandins and leukotrienes: in this way it reduces the entity of the inflammation. Curcumin is a molecule endowed with anti-inflammatory activity. It inhibits the expression of numerous pro-inflammatory cytokines, such as TNF-α, IL-8, IL-1β and IL-6, as well as of other proteins associated with inflammation, such as NF-kB, COX-2, STAT3 and MDA. Bromelain, too, is endowed with anti-inflammatory activity, which can act synergistically with the other active ingredients contained in our formulation. Lycopene and Selenium also seem to be endowed with anti-inflammatory activity, which should contribute further to reducing the inflammation associated with prostatitis, as well as benign prostatic hyperplasia.

*Serenoa repens* extract exhibits an antioxidant activity, which might further contribute to protecting prostatic tissue against the damage of oxidative stress. Lycopene and Selenium also exhibit antioxidant activity. Zinc has shown antioxidant activity and its presence would seem to be fundamental for the correct functioning of prostatic tissue. The activity of these last four active ingredients contained in the mixture of compounds and substances and thus in the composition of the present invention leads to a reduction in the oxidative stress that occurs in the event of prostatitis and benign prostatic hyperplasia.

Finally, *Serenoa repens* extract is capable of blocking $\alpha_1$ receptors and muscarinic receptors, thereby inhibiting smooth muscle contraction and exerting a myorelaxant activity that may contribute to alleviating the symptoms of benign prostatic hyperplasia.

The synergistic action takes place between *Serenoa repens* (Batram) Small., Bromelain, Curcumin, Zinc, Lycopene and Selenium.

The synergism is obtained when *Serenoa repens* (Batram) Small. is present in an amount by weight comprised from 200 mg to 600 mg, Bromelain is present in an amount by weight comprised from 10 mg to 400, Curcumin is present in an amount by weight comprised from 50 mg to 500 mg, Zinc is present in an amount by weight comprised from 10 mg to 20 mg, Lycopene is present in an amount by weight comprised from 1 mg to 10 mg and Selenium is present in an amount by weight comprised from 20 μg to 100 μg.

Advantageously, the preferred dose is the one having the features indicated as 1-dose in Table 1.

EXPERIMENTAL PART

Several studies were conducted on the composition of the present invention for use in the treatment of prostatitis and benign prostatic hyperplasia.

The effect of the composition of the present invention as described above and of the individual constituents making it up were evaluated with the aim of observing the synergistic effect among the individual components on the:

(i) production of pro-inflammatory cytokines and chemokines by prostate epithelial cells;
(ii) proliferation of prostate epithelial cells,
(iii) anti-inflammatory action in mouse models of prostatitis.

Materials and Methods (In Vitro Test on Inflammation Markers)

Normal prostate epithelial cells (PrEC) were maintained at a temperature of 37° C. in a humidified atmosphere made up of 95% air and 5% $CO_2$. The cell culture was kept in an Eagle culture medium supplemented with 10% of heat-inactivated foetal bovine serum (FBS), 2 mM glutamine solution, 100 U/mL of penicillin and 100 μg/mL of streptomycin. As an alternative it is possible to use a specific medium for the culture of prostate epithelial cells.

For the experiments, the cells were seeded in a Petri dish and kept in an incubator for tissue cells. The PrEC cells were treated for 24 hours with TNF-α, at concentrations comprised between 5 and 20 ng/mL, before extracting the RNA to analyse it.

Materials and Methods (In Vitro Test on Cell Proliferation)

Normal prostate epithelial cells (PrEC) were maintained at a temperature of 37° C. in a humidified atmosphere made up of 95% air and 5% $CO_2$. The cell culture was kept in an Eagle culture medium supplemented with 10% of heat-inactivated foetal bovine serum (FBS), 2 mM glutamine solution, 100 U/mL of penicillin and 100 μg/mL of streptomycin. As an alternative it was possible to use a specific medium for the culture of prostate epithelial cells.

The cells were seeded in a Petri dish and covered with 5 mL of culture medium.

Materials and Methods (In Vivo Test)

Wistar rats were used for the study. The animals were housed in temperature-controlled rooms (temperature of 23±2° C., humidity 40-70%, 12-hour light-dark cycles) and had free access to water and food (consisting of a standard diet). The rats were castrated under anaesthesia induced by diethyl ether. Subsequently, the rats were treated subcutaneously with a solution of 17β-extradiol in sesame oil at a dose of 0.25 mg/2 mL/kg, as an inducer of prostatitis. The treatment was performed for a period of 30 days starting from the first day after the castration [1].

Production of Pro-Inflammatory Cytokines and Chemokines In Vitro

The expression of TNF-α, IL-8, IL-1β and IL-6 can be assessed by Western Blot, according to the method described by Cho et al. [2].

The cells were divided into 3 groups:
The first group was treated with the culture medium alone;
The second group was treated with the culture medium containing: *Serenoa repens* extract, Zinc, Selenium and Lycopene;
The third group was treated with the culture medium containing: *Serenoa repens* extract, Zinc, Selenium, Lycopene, Curcumin and Bromelain.

After the treatment with the different culture media, the cells were collected for Western Blot analysis. The whole cell extracts were prepared using a lysis buffer [10 mM Tris (pH 7.4), 5 mM EDTA, 130 mM NaCl, 1% Triton X-100, phenylmethylsulphonyl fluoride (PMSF, 10 mg/ml), aprotinin (10 mg/ml), leupeptin (10 mg/ml), 5 mM phenanthroline and 28 mM benzamidine hydrochloride].

In order to determine the phosphoproteins, the cells were washed with saline solution, buffered with phosphates containing 1 mM of $Na_3VO_4$ and 1 mM of NaF and lysed in a buffer [20 mM Tris-CI (pH 8.0), 137 mM NaCl, 10% glycerol, 1% Triton X-100, 1 mM $Na_3VO_4$, 1 mM NaF, 2 mM EDTA, 200 nM aprotinin, 20 μM leupeptin, 50 μM phenanthroline, 280 μM benzamidine hydrochloride]. In order to isolate the nuclear proteins, the cells were lysed in a hypotonic buffer at a temperature of 0° C. for 20 minutes and centrifuged at 12000 rpm for 10 minutes. The supernatant contains the cytosolic fraction. The pellets were homogenised in a nuclear extraction buffer [10 mM Tris-CI (pH 7.5), 0.5 M NaCl, 2.5% glycerol, 1.5 mM $MgCl_2$, 0.5 mM EDTA, 0.5 mM EGTA, 1 mM DTT, 2 mM PMSF, 200 nM aprotinin] at a temperature of 0° C. for 20 minutes. They were subsequently centrifuged at 12000 rpm for 10 minutes. The supernatant contains the nuclear fraction.

The protein concentration of the extracts was estimated with Bradford reagent, using serum albumin as the standard. The proteins were separated by electrophoresis on polyacrylamide gel, containing 10-12% sodium dodecyl sulphate (SDS-PAGE). The proteins were subsequently transferred onto a nitrocellulose membrane. The membrane was washed with a saline solution buffered with Tris (10 mM Tris, 150 mM NaCl), containing Tween-20 (known as the TBST mixture) and blocked in TBST containing 5% fat-free dried milk. The membrane was incubated with various antibodies to enable recognition of the proteins. The membrane was subsequently incubated with secondary antibodies, coupled with horseradish peroxidase and finally developed with chemoluminescent reagents (ECL, enhanced chemoluminescence western detection reagents).

Cell Proliferation
The cells were divided into three groups:
The first group was treated only with the culture medium having a low content of growth factors;
The second group was treated with the culture medium having a low content of growth factors and containing: *Serenoa repens* extract, Zinc, Selenium and Lycopene;

The third group was treated with the culture medium having a low content of growth factors and containing: *Serenoa repens* extract, Zinc, Selenium, Lycopene, Curcumin and Bromelain.

After 48 hours, the synchronised cells were again stimulated with the culture medium containing normal concentrations of growth factors and the active ingredients, where present. After 12 hours, the cells were subjected to trypsinization and centrifuged. The pellet was resuspended in 1 mL of saline phosphate buffer and 100 µL of the suspension were used for the cell count, using the exclusion test with Trypan Blue. The remaining cells were washed with 4 mL of saline phosphate buffer, again centrifuged and resuspended in 0.5 mL of saline phosphate buffer. After the addition of the cell suspension to 4.5 mL of ethanol at a temperature of 0° C., the samples were frozen at a temperature of –20° C. For the analysis by flow cytometry, the samples were centrifuged for 5 minutes at 200 G, washed with 5 mL of saline phosphate buffer and then resuspended in a staining solution. The analysis was carried out after 30 minutes of incubation at room temperature. The cells were analysed by flow cytometry. Specific software was used to assess the distribution of cells in the various stages of the cell cycle.

Production of Pro-Inflammatory Cytokines and Chemokines In Vivo

The rats were divided into 4 groups:
a group of normal rats, to which a placebo was administered;
a rat prostatitis model group, to which a placebo was administered;
a rat prostatitis model group, to which a formulation containing: *Serenoa repens* extract, Lycopene, Selenium and Zinc was administered;
a rat prostatitis model group, to which a formulation containing: *Serenoa repens* extract, Lycopene, Selenium, Zinc, Curcumin and Bromelain was administered.

After one week of treatment the concentrations of TNF-α, IL-8 and IL-6 in the plasma and prostatic tissues were calculated [3].

Weight and Histological Examination.

After the last treatment dose had been administered and a blood sample had been taken in order to be able to calculate the concentration of pro-inflammatory cytokines, the rats were sacrificed. The prostates were extirpated and weighed. A relative weight was calculated using the following formula:

$$\text{Relative weight} \frac{\text{Prostate weight}}{\text{Animal weight}}$$

After all the prostates had been fixed in a 10% formalin solution, buffered to a neutral pH, each prostate was cut into sections. At this point the tissue samples were dehydrated and incorporated in paraffin. The prostate sections (3-4 mm thick) were stained with haematoxylin-eosin (HE), periodic acid-Shiff (PAS) reagent and Masson's trichrome stain. Each sample was evaluated from a histopathological viewpoint. In order to assess cell damage, the epithelial acinar cells were classified based on a score, which was assigned using the following criteria: columnar shape (2 points), cuboidal shape (1 point), shape similar to a squamous one (0 points) [1].

In order to assess the presence of inflammation, a score was assigned based on the presence of histological signs of inflammation: oedema, haemorrhaging and leukocyte infiltration. Each of these factors was assigned a score from 0 to 3, based on its entity (0 points=none; 3 points=maximum). The 3 scores were then added together in order to quantitatively determine the effect of the inflammation. Total scores of less than 2 were classified as mild inflammation, scores between 2 and 4 were classified as moderate inflammation, and scores above 5 were classified as severe inflammation [4].

Finally, it was possible to determine stromal proliferation. For this purpose all the areas of the samples and the glandular area were measured using a microphotograph digitiser. This enables the stromal ratio to be calculated [1].

REFERENCES

[1] T. Kamijo, S. Sato, and T. Kitamura, "Effect of cernitin pollen-extract on experimental nonbacterial prostatitis in rats," *Prostate*, vol. 49, no. 2, pp. 122-131, October 2001.

[2] J.-W. Cho, K.-S. Lee, and C.-W. Kim, "Curcumin attenuates the expression of IL-1beta, IL-6, and TNF-alpha as well as cyclin and in TNF-alpha-treated HaCaT cells; NF-kappaB and MAPKs as potential upstream targets.," *Int. J. Mol. Med.*, vol. 19, no. 3, pp. 469-474, 2007.

[3] Q.-Y. Zhang, Z.-N. Mo, and X.-D. Liu, "[Reducing effect of curcumin on expressions of TNF-alpha, IL-6 and IL-8 in rats with chronic nonbacterial prostatitis].," *Zhonghua Nan Ke Xue*, vol. 16, no. 1, pp. 84-8, January 2010.

[4] K. E. Rippere-Lampe, M. Lang, H. Ceri, M. Olson, H. A. Lockman, and A. D. O'Brien, "Cytotoxic necrotizing factor type 1-positive *Escherichia coli* causes increased inflammation and tissue damage to the prostate in a rat prostatitis model," *Infect. Immun.*, vol. 69, no. 10, pp. 6515-6519, 2001.

The invention claimed is:

1. A method of treatment of disorders or diseases or pathologies connected to or deriving from prostatitis and/or benign prostatic hyperplasia, wherein said method of treatment comprises administering a therapeutically effective amount of a composition comprising a mixture of *Serenoa repens* (W. Batram) Small., Bromelain, Curcumin, Zinc, Lycopene, and Selenium to a subject in need thereof.

2. The method according to claim 1, wherein the *Serenoa repens* (W. Batram) Small. is present in said mixture in an amount by weight of 200 mg to 600 mg.

3. The method according to claim 1, wherein the Bromelain is present in said mixture in an amount by weight of 10 mg to 400 mg.

4. The method according to claim 1, wherein the Curcumin is present in said mixture in an amount by weight of 50 mg to 500 mg.

5. The method according to claim 1, wherein the Zinc is present in said mixture in an amount by weight of 12 mg to 18 mg.

6. The method according to claim 1, wherein the Lycopene is present in said mixture in an amount by weight of mg to 10 mg.

7. The method according to claim 1, wherein the Selenium is present in said mixture in an amount by weight of 20 ug to 100 ug.

8. The method according to claim 1, wherein said composition is in the form of softgel capsules.

9. The method according to claim 1, wherein said composition comprises the following:

| Active ingredient | 1-Dose |
| --- | --- |
| *Serenoa repens*, phytosterolic extract | 400 mg |
| Bromelain | 150 mg |
| Curcumin | 100 mg |
| Zinc | 15 mg |
| Lycopene | 6 mg |
| Selenium | 41.5 µg. |

10. The method according to claim 1, wherein the *Serenoa repens* (W. Batram) Small. is present in said mixture in an amount by weight of 300 mg to 500 mg.

11. The method according to claim 1, wherein the Bromelain is present in said mixture in an amount by weight of 120 mg to 180 mg.

12. The method according to claim 1, wherein the Curcumin is present in said mixture in an amount by weight of 75 mg to 150 mg.

13. The method according to claim 1, wherein the Zinc is present in said mixture in an amount by weight of 15 mg.

14. The method according to claim 1, wherein the Lycopene is present in said mixture in an amount by weight of 3 mg to 8 mg.

15. The method according to claim 1, wherein the Selenium is present in said mixture in an amount by weight of 40 pg to 60 ug.

16. The method according to claim 1, wherein
the *Serenoa repens* is obtained by supercritical extraction from fruit at a concentration of least 90% in a sterolic lipid extract,
the Lycopene is extracted from the fruit of *Solanum lycopesicum*,
the Bromelain is a composition comprising the bromelain enzymes or is an extract of the stem of *Ananas comosus* L. Merr.,
the Zinc is zinc oxide or zinc gluconate or zinc acetate,
the Curcumin is obtained from the rhizome of *Curcuma longa*, and
the Selenium is Selenomethionine or from sodium selenite.

* * * * *